United States Patent [19]
Paolini et al.

[11] Patent Number: 5,954,710
[45] Date of Patent: Sep. 21, 1999

[54] DEVICE AND METHOD FOR ELIMINATING ADIPOSE LAYERS BY MEANS OF LASER ENERGY

[75] Inventors: Cesare Paolini, Montanino Di Reggello; Maurizio Maida, Marina Di Massa; Fabrizio Mencarelli, Fivizzano, all of Italy

[73] Assignee: El.En. S.p.A., Florence, Italy

[21] Appl. No.: 08/798,516

[22] Filed: Feb. 10, 1997

[30] Foreign Application Priority Data

Feb. 13, 1996 [IT] Italy ................ FI96A0025

[51] Int. Cl.⁶ ................................ A61B 5/00
[52] U.S. Cl. ................................ 606/7; 606/15
[58] Field of Search ................ 606/9, 4, 5, 6, 606/7, 13, 14, 15, 16, 17; 128/898

[56] References Cited

U.S. PATENT DOCUMENTS

| | | | |
|---|---|---|---|
| 4,985,027 | 1/1991 | Dressel | 606/15 |
| 5,246,436 | 9/1993 | Rowe | 606/13 |
| 5,281,212 | 1/1994 | Savage et al. | 606/14 |
| 5,282,798 | 2/1994 | Bruse et al. | 606/17 |
| 5,304,167 | 4/1994 | Freiburg | 606/16 |
| 5,312,392 | 5/1994 | Hofstetter | 606/2 |
| 5,370,642 | 12/1994 | Keller | 606/9 |
| 5,445,634 | 8/1995 | Keller | 606/9 |
| 5,466,234 | 11/1995 | Loeb et al. | 606/7 |
| 5,603,710 | 2/1997 | Easley et al. | 606/15 |
| 5,632,739 | 5/1997 | Anderson et al. | 606/15 X |
| 5,643,250 | 7/1997 | O'Donnell, Jr. | 606/4 |
| 5,651,783 | 7/1997 | Reynard | 606/4 |
| 5,655,544 | 8/1997 | Johnson | 128/898 |

*Primary Examiner*—Robert L. Nasser
*Attorney, Agent, or Firm*—McGlew and Tuttle, P.C.

[57] ABSTRACT

The device for the removal of subcutaneous adipose layers comprises a first laser source (1), optical fiber conveying means (3) for conveying the laser beam emitted by said first source (1) and a hollow needle (7) for guiding the fiber, said fiber ending in the vicinity of the end of the needle.

8 Claims, 1 Drawing Sheet

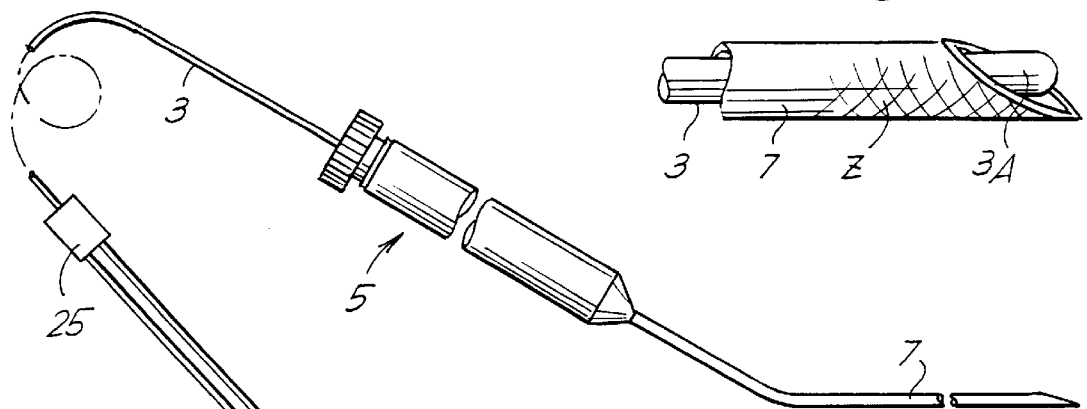
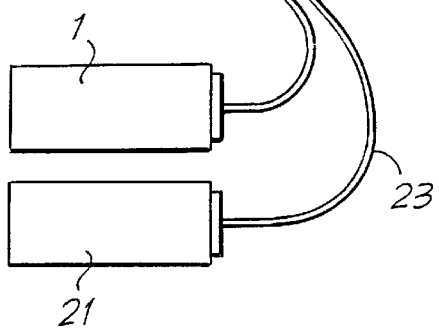
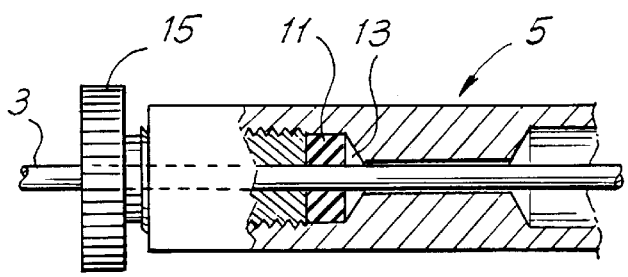
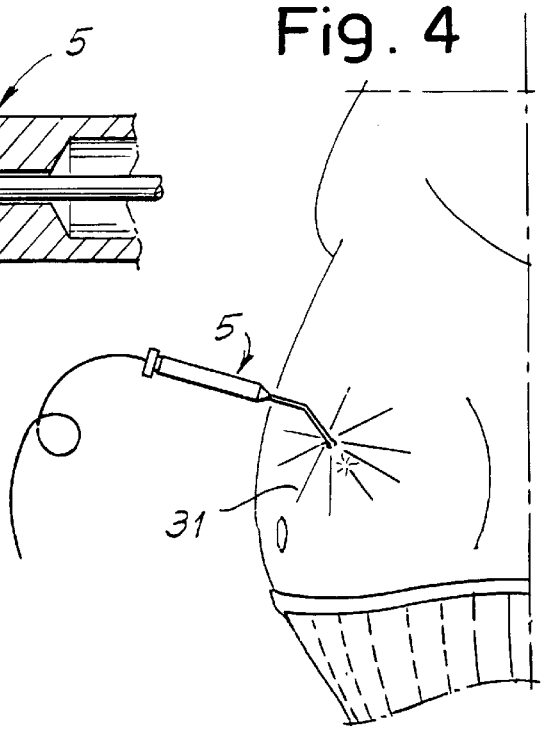

… …

DEVICE AND METHOD FOR ELIMINATING ADIPOSE LAYERS BY MEANS OF LASER ENERGY

DESCRIPTION

1. Field of the invention

The present invention relates to a device for eliminating adipose layers and to an associated technique for carrying out this elimination using said device.

2. Prior art

The reduction of subcutaneous adipose layers constitutes one of the most important areas of aesthetic treatments.

Two techniques currently exist for this purpose. The first technique, known as liposuction, consists of introduction into the adipose layers of probes roughly 5 mm in diameter through holes made in the skin of the patient undergoing treatment, for suction and removal of fat. This technique has a number of disadvantages, such as the creation of a lack of homogeneity in the form of depressions in the zone of insertion of the probe which are visible from the outside, as well as excessive bleeding of the patient undergoing treatment. Furthermore, both the cells of fat and the stroma are sucked out non-selectively.

The second technique utilizes subcutaneous ultrasonic probes to rupture the membrane of the adipose cells, thus causing the escape of liquid which then has to be sucked out subsequently. In this case, suction of the stroma is not brought about and bleeding is therefore more limited. However, the disadvantage of the lack of homogeneity of the treatment remains.

AIMS OF THE INVENTION

The aim of the present invention is to produce a device and an associated method for eliminating adipose layers which do not have the disadvantages mentioned above.

In particular, a first aim of the present invention is the production of a device and a method which allow uniform treatment.

A further aim is the production of a device and a method which allow selective elimination of the adipose cells without damaging the stroma.

Yet another aim of the present invention is the production of a device and a method which eliminate the problem of bleeding and which reduce the dimensions of the holes for insertion of the probes.

SUMMARY OF THE INVENTION

These and other aims and advantages, which will be clear to experts in the field from reading the text which follows, are obtained essentially with a device which comprises a first laser source, optical fiber conveying means for conveying the laser beam emitted by said first source, and a hollow needle for guiding the fiber, said fiber ending in the vicinity of the end of the needle.

With this device, it is possible to implement a method for the reduction of subcutaneous adipose layers, on the basis of introducing into said subcutaneous adipose layers a laser beam at an intensity and at a wavelength which are such that the lipolysis of the adipose cells is brought about, that is a rupturing of the membranes of the cells themselves, with consequent transformation of the adeps into a liquid substance which is then sucked out or preferably left in place in order to be drained by the lymphatic system and by the action of the phagocytes. In addition to a clear reduction in traumatism and greater selectivity of the method implemented in this manner in comparison with the liposuction system, the advantage is also obtained that the energy of the laser beam can be used to cauterize the small blood vessels which may be damaged by the insertion of the needle into the adipose layers. Loss of blood is thus virtually completely eliminated.

In practice, the needle is borne by a hand unit which, in order to be more easily maneuverable, is inclined in relation to the needle.

In addition to a laser source which emits at a wavelength and at a power which are such that lipolysis is brought about, it is possible, with the same optical fiber, or with an additional optical fiber guided in the same needle, to convey into the adipose layers a beam of visible light which makes possible transcutaneous vision during implementation of the method.

Further advantageous characteristics of the device and the method according to the invention will be described below.

BRIEF DESCRIPTION OF THE DRAWINGS

The invention will be better understood by following the description and the attached drawing which shows a non-limiting exemplary embodiment of the invention itself and in which:

FIG. 1 shows a diagram of the device;

FIG. 2 shows an enlarged longitudinal section of the hand unit of the device in FIG. 1;

FIG. 3 shows an enlargement of the point of the needle, and

FIG. 4 illustrates the use of the device in an example of application.

DETAILED DESCRIPTION OF THE INVENTION

With reference initially to FIG. 1, the device comprises a laser source 1 of the NdYAG type, with which an optical fiber 3 is associated, which conveys the energy of the source 1 toward a hand unit 5 equipped with a hollow guide needle 7 with a beveled end (FIG. 3). The needle has an external diameter of, for example, roughly 1 mm. The terminal end 3A of the optical fiber 3 ends at the point of the needle.

In the example illustrated, the needle has an inclination in relation to the hand unit 5 of roughly 10–30 degrees and preferably 15–20° to facilitate its use.

In FIG. 2, a possible system of fixing the fiber 3 can be seen, which comprises an elastic sleeve 11 accommodated in a seat 13, through which the fiber 3 passes and which is clamped by means of a threaded ring nut 15.

In the example illustrated, the device comprises a second laser source 21 which emits radiation in the visible range which is conveyed by means of a second optical fiber 23 to a connector 25, in which the visible radiation emitted by the laser 21 is introduced into the fiber 3. In this manner, the optical fiber 3 conveys to the point of the needle 7 a laser beam in the visible range also which allows the operator, in reduced ambient light, to follow accurately (by transcutaneous vision permitted by the transparency of the skin) the position of the end of the fiber and therefore to control the instantaneous point of application of the laser energy generated by the source 1.

The laser source 1 emits a beam which is preferably pulsed, at a wavelength between 0.75 and 2.5 micrometers, for example at 1.06 micrometers, with an energy level between 30 and 300 mjoules per pulse. The wavelength is preferably between 0.8 and 1.1 micrometers.

The device described above is used as follows: the fiber is inserted subcutaneously into the patient, in the adipose layer to be eliminated. The end of the fiber 3 thus comes directly into contact with the adipose layer. The laser beam, in the appropriate dosage, brings about the rupturing of the membranes of the adipose cells and at the same time cauterizes the very small veins contained in the stroma, which can be easily damaged by the penetration of the needle 7. In this manner, the adeps becomes liquid and at the same time a local hemostasis is created. The liquefied fat is then absorbed by the body by lymphatic drainage and the action of the phagocytes, while subsequent intervention, similar to that carried out in the case of treatment with ultrasonic probes, to remove the liquefied fat is not ruled out.

In practice, the needle 7 is initially inserted subcutaneously and is then moved forward and backward by the operator for the time which is necessary according to the characteristics of the tissue also and which is easily determined by the operator. Typically, to achieve the lipolysis of an adequate quantity of adipose cells, treatment with an energy level of 100 mjoules for a time of 200 microseconds per pulse is appropriate; the needle is kept in each penetration hole for a few minutes.

The movement of the point of the needle is easily controlled by means of the transcutaneous vision allowed by the visible laser beam generated by the second source 21. Lipolysis action is thus brought about in a certain portion of tissue. By extracting the needle and inserting it subcutaneously in an adjacent position, a subsequent portion of tissue is treated. From one and the same entry hole, the needle 7 can be inserted in various radial directions, treating an entire area of the tissue, as can be seen in FIG. 4, where 31 indicates in broken lines as a guide the insertion lines of the needle 7.

The end part of the needle 7 can be knurled in order to cause, during penetration of the adipose layers, a rupturing of the adipose cells and therefore in order to obtain greater effectiveness of treatment. In FIG. 3, the knurling is indicated diagrammatically by Z.

It is intended that the drawing shows only an example given only by way of practical demonstration of the invention, it being possible for the invention to vary in form and arrangement without moreover leaving the scope of the concept which forms the invention itself. Any presence of reference numbers in the enclosed claims has the purpose of facilitating reading of the claims with reference to the description and to the drawing, and does not limit the scope of protection represented by the claims.

We claim:

1. A device for the removal of subcutaneous adipose layers, the device comprising:

a hollow needle with a sharp tip forming piercing means for mechanically piercing skin of a patient and the adipose layers said hollow needle having curling at an end part;

a laser source means including a laser source having emitting characteristics for generating a laser beam that causes the lipolysis of adipose cells to transform the adipose cells into a liquid; and optical fiber means including an optical fiber connected to said laser source and connected to said needle to convey the laser beam from said source toward said sharp tip of said needle.

2. The device as claimed in claim 1, further comprising a hand unit connected to said needle, said optical fiber means being positioned inside said hollow needle for emitting said laser beam out of an inside of said hollow needle.

3. The device as claimed in claim 1, wherein said laser source means emits at a wavelength between 0.75 and 2.5 micrometers, and at an energy level between 30–300 mjoules per pulse.

4. The device as claimed in claim 1, wherein said laser source means emits a pulsed beam with an energy level between 30 and 300 mjoules per pulse.

5. The device as claimed in claim 1, further comprising:

another laser source means having an another laser source with emitting characteristics for generating a laser beam in the visible range; and conveying means for conveying the light emitted by said another laser source to said end of said needle.

6. The device as claimed in claim 5, wherein said conveying means includes another optical fiber.

7. The device as claimed in claim 6, wherein said another optical fiber is connected to said optical fiber at a location spaced from said sharp tip, said optical fiber exclusively conveying beams generated by said laser source and said another laser source form said location toward said sharp tip of said needle.

8. The device as claimed in claim 1, wherein said laser source means emits at a wavelength between 0.75 and 2.5 micrometers and at an energy level of 100 mjoules for 200 microseconds.

\* \* \* \* \*